(12) United States Patent
Pardes et al.

(10) Patent No.: US 7,997,460 B2
(45) Date of Patent: *Aug. 16, 2011

(54) CONTINUOUSLY SEALING ONE WAY VALVE ASSEMBLY AND FLUID DELIVERY SYSTEM AND FORMULATIONS FOR USE THEREIN

(75) Inventors: Greg Pardes, New York, NY (US); Stewart Swiss, Lloyd Harbor, NY (US); Ilan Hofman, Dollard des Ormeaux (CA); Wesley Domareki, Port Murray, NJ (US)

(73) Assignee: ReSeal International Limited Partnership, New York, NY (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/092,691

(22) PCT Filed: Nov. 3, 2006

(86) PCT No.: PCT/US2006/043113
§ 371 (c)(1),
(2), (4) Date: Feb. 18, 2009

(87) PCT Pub. No.: WO2007/056233
PCT Pub. Date: May 18, 2007

(65) Prior Publication Data
US 2009/0152306 A1 Jun. 18, 2009

Related U.S. Application Data

(63) Continuation-in-part of application No. 11/267,868, filed on Nov. 3, 2005, now Pat. No. 7,306,129.

(60) Provisional application No. 60/783,451, filed on Mar. 17, 2006, provisional application No. 60/783,569, filed on Mar. 17, 2006, provisional application No. 60/840,377, filed on Aug. 24, 2006.

(51) Int. Cl.
*B65D 5/72* (2006.01)

(52) U.S. Cl. ........ 222/494; 222/105; 222/212; 222/213; 222/326; 222/490; 137/853; 604/213

(58) Field of Classification Search .......... 222/490–491, 222/494–497, 321.7, 380, 420–422, 206–207, 222/212–215, 105, 107, 630–631, 183, 326, 222/386, 94–95, 325, 327, 321.8, 321.9; 137/852–853; 604/298, 213
See application file for complete search history.

(56) References Cited

U.S. PATENT DOCUMENTS

| | | | | |
|---|---|---|---|---|
| 2,715,980 | A * | 8/1955 | Frick | 222/183 |
| 3,124,275 | A * | 3/1964 | Lake | 222/182 |
| 3,506,163 | A * | 4/1970 | Rauh et al. | 222/212 |
| 3,739,652 | A * | 6/1973 | Caldwell et al. | 74/421 A |
| 4,349,133 | A * | 9/1982 | Christine | 222/183 |
| 4,387,734 | A * | 6/1983 | Borsanyi | 137/206 |
| 4,397,132 | A * | 8/1983 | Pardes et al. | 53/471 |
| 4,413,757 | A * | 11/1983 | Adler | 222/105 |

(Continued)

*Primary Examiner* — Frederick C. Nicolas
(74) *Attorney, Agent, or Firm* — Kramer Levin Naftalis & Frankel LLP

(57) ABSTRACT

A reusable continuously sealing one-way valve assembly and delivery system flows a sterile flowable substance from a source to an outlet orifice and prevents any backflow of contaminants through the continuously sealing one way valve assembly when the flowable substance ceases to flow. The valve assembly includes an elastomeric membrane which aids in preventing any backflow of contaminants when dispensing of the flowable substance is stopped. Multiple dosing of preservative-free flowable substance is provided.

49 Claims, 8 Drawing Sheets

U.S. PATENT DOCUMENTS

| | | | |
|---|---|---|---|
| 4,415,121 A * | 11/1983 | Berger et al. | 239/229 |
| 4,421,510 A * | 12/1983 | Ahlbeck | 604/323 |
| 4,846,810 A * | 7/1989 | Gerber | 604/247 |
| 4,898,306 A * | 2/1990 | Pardes | 222/206 |
| 5,080,138 A * | 1/1992 | Haviv | 137/853 |
| 5,092,855 A * | 3/1992 | Pardes | 604/247 |
| 5,190,190 A * | 3/1993 | Fudalla | 222/105 |
| 5,305,786 A * | 4/1994 | Debush | 137/512.3 |
| 5,836,484 A * | 11/1998 | Gerber | 222/494 |
| 6,325,253 B1 * | 12/2001 | Robinson | 222/212 |
| 6,386,395 B1 * | 5/2002 | Lunghetti | 222/213 |
| 6,536,631 B1 * | 3/2003 | Nickels et al. | 222/212 |
| 6,662,977 B2 * | 12/2003 | Gerber et al. | 222/494 |
| 6,695,173 B1 * | 2/2004 | Fontana | 222/212 |
| 6,766,816 B2 * | 7/2004 | Secondo | 137/1 |
| 6,896,151 B1 * | 5/2005 | Robinson | 222/1 |
| 6,997,219 B2 * | 2/2006 | Py et al. | 141/314 |
| 7,077,176 B2 * | 7/2006 | Py | 141/301 |
| 7,152,759 B2 * | 12/2006 | Walton | 222/146.6 |
| 7,226,237 B2 * | 6/2007 | Ceccarelli | 404/6 |
| 7,306,129 B2 * | 12/2007 | Swiss et al. | 222/494 |
| 7,513,396 B2 * | 4/2009 | Pardes et al. | 222/494 |
| 7,544,671 B2 * | 6/2009 | Karageozian et al. | 514/54 |

* cited by examiner

EXIT FLOW PATH

ENTRY FLOW PATH

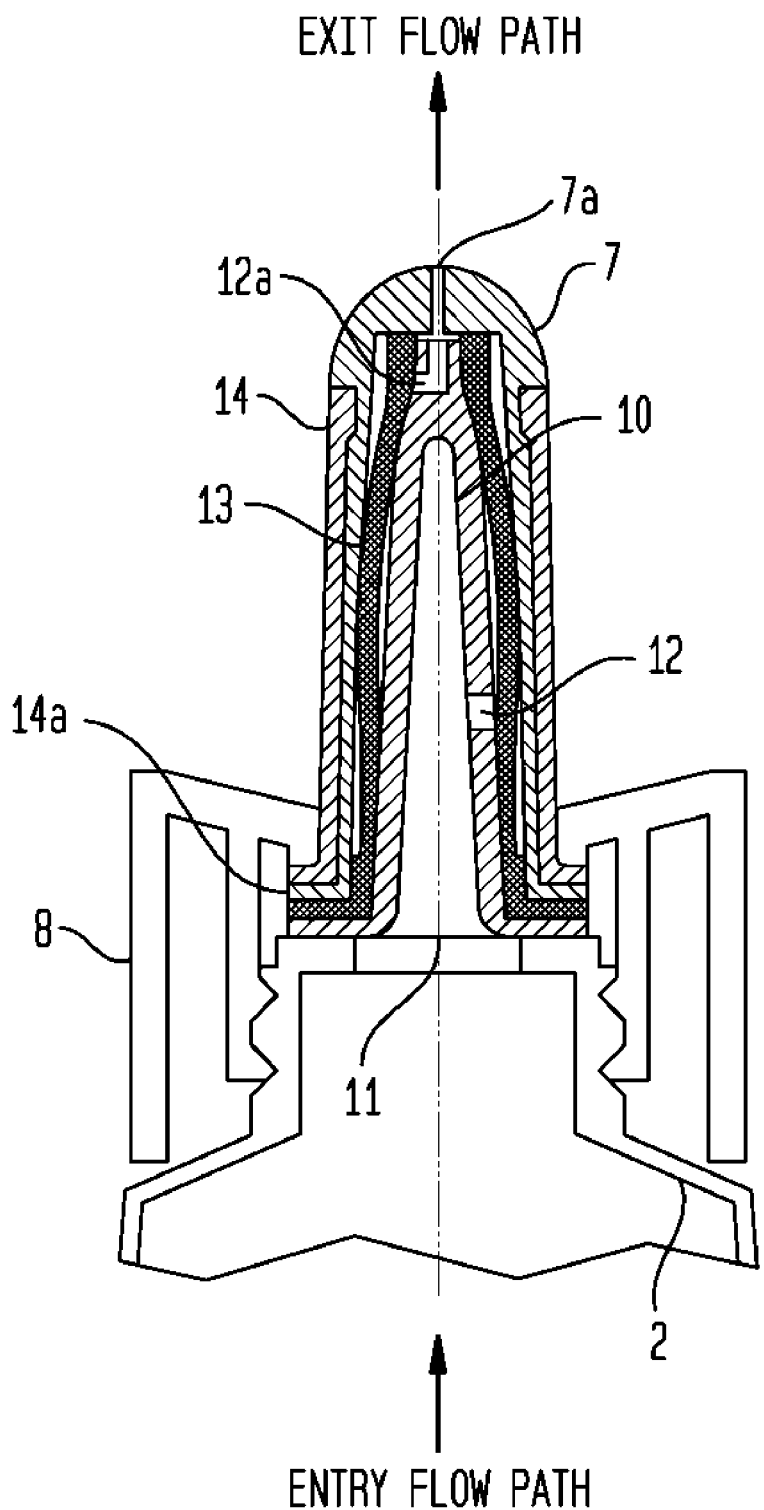

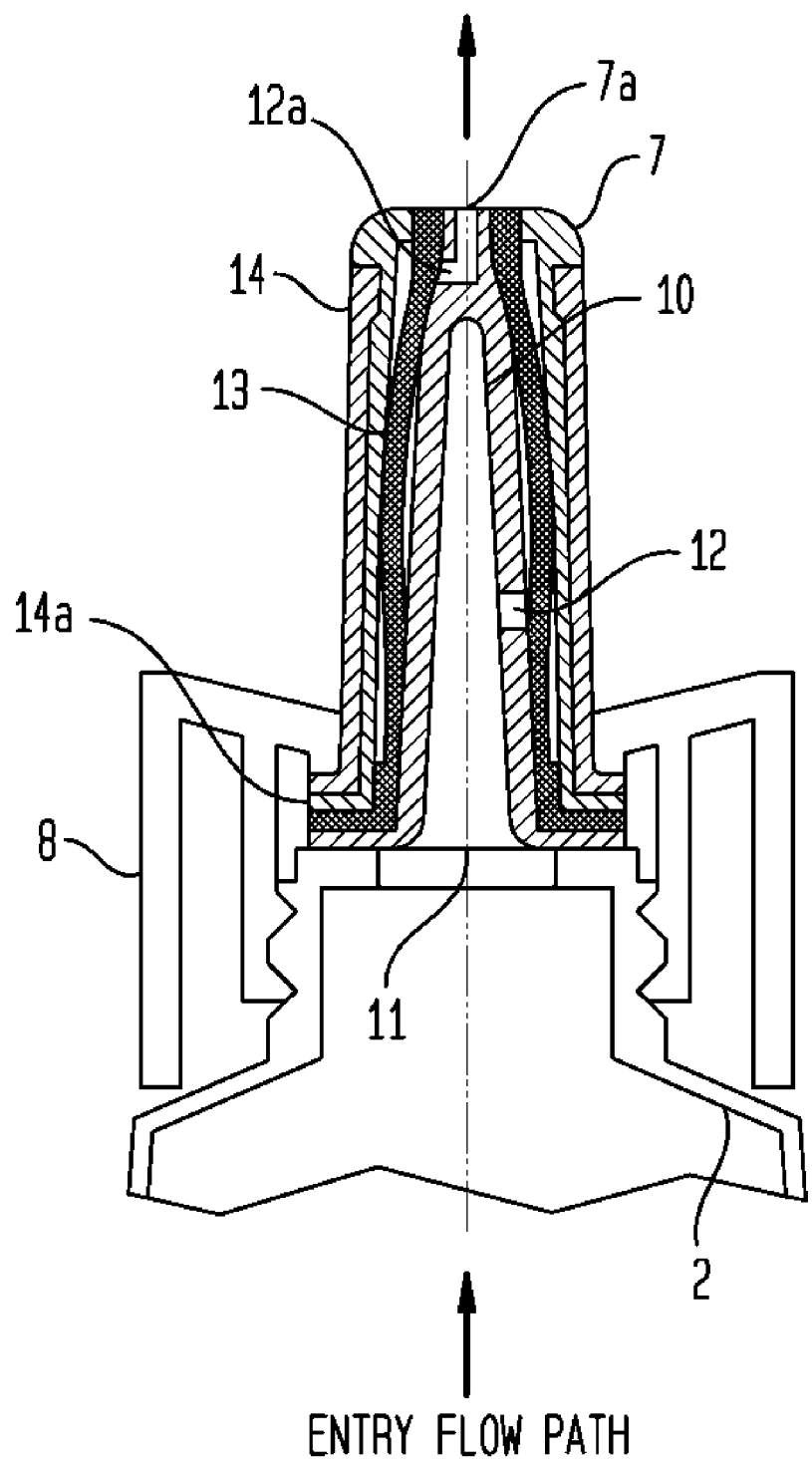

CONTINUOUSLY SEALING ONE WAY VALVE ASSEMBLY AND FLUID DELIVERY SYSTEM AND FORMULATIONS FOR USE THEREIN

CROSS-REFERENCE TO RELATED APPLICATIONS

This application is the United States national phase filing of the corresponding international application number PCT/US2006/043113, filed on Nov. 3, 2006, which is a continuation-in-part of U.S. patent application Ser. No. 11/267,868, filed Nov. 3, 2005, now U.S. Pat. No. 7,306,129 and which claims benefit of U.S. Provisional Patent Application Ser. Nos. 60/783,451, filed Mar. 17, 2006; 60/783,569, filed Mar. 17, 2006; and 60/840,377, filed Aug. 24, 2006, each of which is incorporated by reference herein in its entirety.

FIELD OF THE INVENTION

The present invention is directed to a dispensing and delivery system including a continuously sealing one way valve assembly for dispensing a sterile flowable substance, which can include preservatives or be preservative free, while preventing a backflow of contaminants into the source of the flowable substance. The dispensing and delivery system includes, for example, a valve assembly enclosed by a pressure displaceable flexible member or elastomeric member for effecting the passage of the flowable substance to a controllable outlet, while preventing any backflow to the source of the flowable substance after dispensing individual portions or doses of the flowable substance.

BACKGROUND INFORMATION

In the past, to maintain the flowable substance free of contaminants, preservatives have been mixed in with the flowable substance in the reservoir from which it is to be dispensed. The use of preservatives tends to be detrimental to users and often limits the effectiveness of the flowable substance, particularly when the flowable substance is a pharmaceutical such as an eye care solution, an intranasal drug, cosmetic treatment or skin treatment product. This group of prescription and nonprescription medications are often formulated with preservatives in multi-dose formats. The flowable substance may also be a food stuff, a beverage, a nutraceutical or cosmeceutical product.

Another consideration is the ability of the valve assembly to deliver a selected amount of the flowable substance to the outlet without causing any damage to the user, such as when applying an eye care solution directly into the eye.

In the past, flexible membranes have been used to control the flow of the flowable substance to the valve assembly outlet while preventing any backflow to the source of the flowable substance. However such valves, such as the valve described in U.S. Pat. No. RE34,243, which is incorporated by reference herein in its entirety, describe the use of O-rings in conjunction with a uniformly thick flexible membrane to effect a seal. Other valve assemblies also used cylindrical parts which required, for example, sliding the pretensioned flexible membrane over the straight sided core during assembly, preventing automated high speed assembly. Therefore, an effectively designed valve assembly which was able to be manufactured, for example via high speed automated production, and limited the costs of manufacture by reducing component parts and allowing the use of high speed automated production, was not provided in the past.

SUMMARY OF THE INVENTION

According to an exemplary embodiment of the present invention, a dispensing and delivery system conveys a flowable substance from a closed source, such as a collapsible reservoir, while preventing any backflow of oxygen or other contaminants from the ambient atmosphere through the valve assembly and into the source of the flowable substance after a portion of the substance has been dispensed.

The collapsible reservoir can be, for example, a bellows type reservoir, a collapsible tube, an internal bag or other type of suitable reservoir designed to dispense practically all of its contents. According to an exemplary embodiment of the present invention, the dispensing delivery system has a normally closed controllable outlet orifice for dispensing a controlled amount of the flowable substance out of the valve assembly. The reservoir is in sealed contact with the valve assembly so that its contents do not receive any contaminants when the flowable substance is dispensed.

Dispensation of the flowable substance is effected by applying pressure to the reservoir directly or through a pump so that its contents flow to and through the valve assembly. The contents may be a pharmaceutical, such as eye care solutions and/or gels or nasal solutions and/or gels which must be kept free of contaminants during dispensing. According to an exemplary embodiment of the present invention, a multiple number of dispensed amounts can be provided while keeping the undispensed flowable substance preservative-free. The reservoir is protected by a housing so that pressure is not accidentally applied.

The valve assembly includes, for example, an axially extending structure open to the dispenser or reservoir of the flowable substance. The valve assembly can be formed of an axially extending inner core open to the reservoir and formed of a rigid plastic component. The interior of the core can have a passageway for receiving the flowable substance from the reservoir. At least one port extending from the passageway can be provided and affords an opening for conveying the flow substance out of the inner core. The inner core can be designed with a substantially tapered or substantially conical shape.

An axially extending flexible membrane tightly encloses the inner core and covers the outlet end of the port through the inner core. The flexible membrane moves outwardly from the inner core when the flowable substance is pressurized and passes through the port and flows toward the outlet end of the flexible membrane. The flexible membrane is structured such that it is, for example, thicker at the end closest to the valve opening, e.g. the flexible membrane is not uniformly thick along its length. This thickness allows the valve to seal at the thicker end first. Alternatively, even if the membrane was of uniform thickness, the elasticity of the membrane can be varied so that the portion of the membrane closest to the valve opening is less elastic, resulting in the portion of the membrane closest to the valve opening closing first.

In exemplary embodiments, the flexible membrane and, as described above, the inner core, are of a substantially tapered or substantially conical shape, allowing for the rapid assembly and natural resting of the flexible membrane over the inner core.

A valve cover located laterally outwardly from the flexible membrane ends at the controllable outlet orifice. The pressurized flowable substance travels between the radially outwardly extended flexible membrane and the outer surface of the inner core and flows to the controllable outlet orifice. The outlet orifice provides for controlled amounts of the flowable substance to be dispensed. An over cap covers the exterior of the valve cover to protect the valve assembly during storage. A collar can join the valve assembly to the reservoir and afford a sealed arrangement preventing any flow of contaminants into the reservoir. The collar and the neck area of the reservoir are designed with locking features that permit the override of the collar during assembly but subsequently prevent the unscrewing and disassembly of the collar and the opening of and likely contamination of the system.

The various features of novelty which characterize the present invention are pointed out with particularity in the claims annexed to and forming a part of this disclosure. For a better understanding of the present invention, its operation, advantages and specific objects attained by its use, reference should be had to the accompanying drawings and descriptive matter in which preferred embodiments of the invention are illustrated and described.

BRIEF DESCRIPTION OF THE DRAWINGS

FIG. 6A is an axially extending partial view of the continuously sealing one way valve assembly with one port and an outlet port according to an exemplary embodiment of the present invention.

FIG. 6B is an enlarged axially extending partial view of the continuously sealing one way valve assembly with one port and an outlet port according to an exemplary embodiment of the present invention.

DETAILED DESCRIPTION OF THE INVENTION

Figure 1:
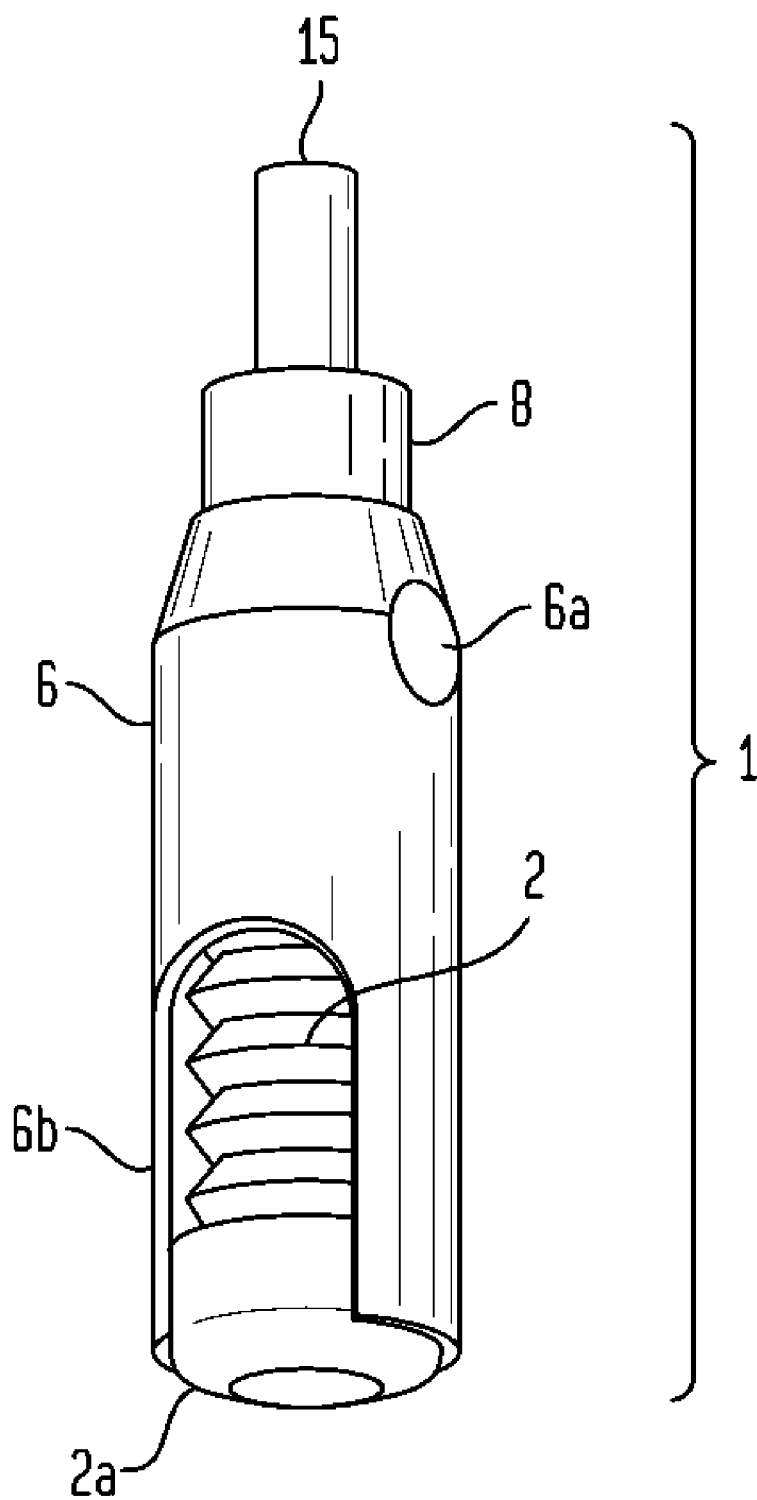
FIG. 1 is an axially extending view of a dispensing and delivery system according to an exemplary embodiment of the present invention.
Figure 2A:
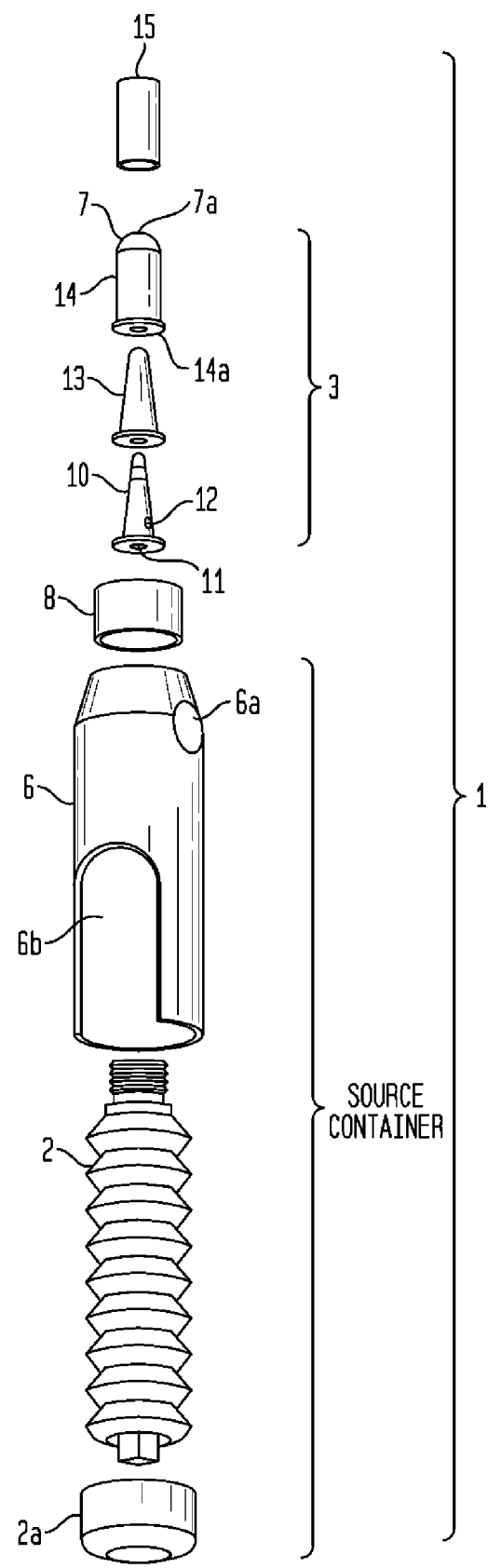
FIG. 2A is an exploded view of a dispensing and delivery system such as that shown in FIG. 1 according to an exemplary embodiment of the present invention.
Figure 2B:
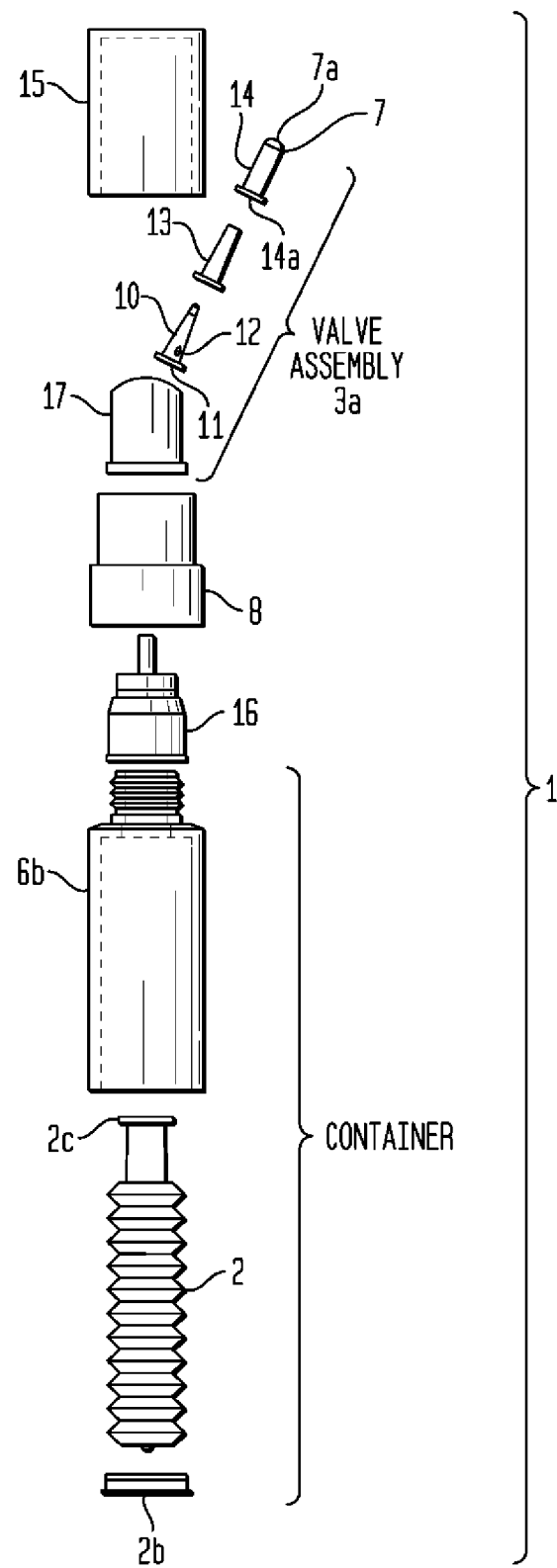
FIG. 2B is an exploded view of a dispensing and delivery system such as that shown in FIG. 1 according to an exemplary embodiment of the present invention which includes a pump for dispensing flowable substance.

As shown in FIGS. 1, 2A and 2B, dispensing and delivery system 1 according to exemplary embodiments of the present invention is comprised of a bellows reservoir or source 2 located within a housing 6. The housing 6 and holds reservoir 2 of flowable substance, preferably a sterile or pure flowable substance, a valve assembly 3 (shown in detail in FIGS. 2A, 2B and 4A-D) for conveying the flowable substance from the reservoir 2 to an outlet when pressure is applied to the reservoir 2 or to an actuator 2a connected to the reservoir 2. An over cap 15 covers the valve assembly 3 to prevent contamination from entering the valve assembly 3 during storage. The housing 6 has surfaces 6a for holding the assembly. A collar 8 connects the valve assembly 3 to the reservoir 2 affording a sealed connection so that ambient contaminants cannot pass into the reservoir 2.

Referring again to FIGS. 1, 2A and 2B, the bellows reservoir 2 is sufficiently large to allow for multiple doses to be dispensed from the reservoir and collapses when pressure is applied to the reservoir. Other suitable reservoirs may be used, such as a collapsible tube or an internal bag in a reservoir that permit multi-dose dispensation of the flowable substance. The valve assembly 3 and collar 8 preferably prevents air or other contamination from entering the reservoir following the dispensing procedure.

Referring yet again to FIGS. 1, 2A and 2B, the bellows reservoir or source 2 is laterally enclosed, for example, by an axially extending housing 6 to prevent the accidental application of pressure to the reservoir. A slot 6b extending axially in the housing 6 permits a user to gain access to an actuator 2a of the reservoir as the flowable substance is pressed out. The housing 6 has surfaces 6a for holding the housing when the flowable substance is being dispensed.

Referring now to FIGS. 2A and 2B, the valve assembly 3 has valve cover 14 which encircles the flexible membrane 13. The valve assembly 3 is comprised of an inner core 10, an axially extending blind passageway 11, ports 12, a flexible membrane 13, a valve cover 14 with a flange 14a, and a soft cover 7 with a controllable outlet orifice 7a (all of which are described in greater detail below in connection with the descriptions of FIGS. 4A-D). While the flexible membrane 13 is hollow so as to accommodate the inner core 10, it is understood that when assembled with the device, it is filled with the inner core 10 such that no gap remains when the valve assembly is at rest.

The end of the valve cover 14 adjacent the reservoir 2 has a radially outwardly extending flange 14a bearing against the flange at the end of the flexible membrane effecting the seal for the valve assembly at the opening from the reservoir 2. The opening or neck area of reservoir 2 seals against flange 14a, for example, by way of a screw thread which mates with the collar 8. Alternatively, or in addition, the collar 8 and the opening or neck area of the reservoir 2 are designed with locking features that permit the override of the collar 8 during assembly but subsequently prevent the unscrewing and disassembly of the collar 8 and the opening of the system. This prevents any unintended contamination by the consumer and also eliminates the possibility of refilling the system.

Referring now especially to FIG. 2B, in an embodiment suitable for pumping flowable substance, a pump assembly 16 is joined to a valve assembly 3a and to a reservoir 2 and bottle 6. The collar 8 surrounds the connection between the pump assembly 16 and valve assembly 3a. The pump assembly 16 is connected to the bottle 6 by screw threads. The opening or neck area of bottle 6 seals against pump assembly 16, for example, by way of a screw thread which mates with the pump assembly 16 sealing flange 2c of reservoir 2 between the bottle 6 and the pump assembly 16. Alternatively, or in addition, the collar 8 and the opening or neck area of the reservoir 2 are designed with locking features that permit the override of the pump assembly 16 during assembly but subsequently prevent the unscrewing and disassembly of the pump assembly 16 and the opening of the system. This prevents any unintended contamination by the consumer and also eliminates the possibility of refilling the system.

The pump assembly 16 is thus connected to a valve assembly 3a having an actuator 17, an inner core 10, an axially extending blind passageway 11, ports 12, a flexible membrane 13, a valve cover 14 with a flange 14a, and a soft cover 7 with a controllable outlet orifice 7a (further described below in connection with the descriptions of FIGS. 4A-D). Optionally, the actuator 17 may be connected to or include an atomizer. In operation the actuator 17 serves to transfer force via a check valve of the pump assembly 16 to draw flowable substance from the reservoir 2, thus providing the force necessary to dispense flowable substance. For example, conventional pumps may be utilized in this manner.

Furthermore, the reservoir 2 can be disposed within a bottle 6 whose open end is sealed by a plug 2c. Plug 2c serves to protect the reservoir 2 from damage, rupture or inadvertent application of force on the reservoir 2.

Figure 3:
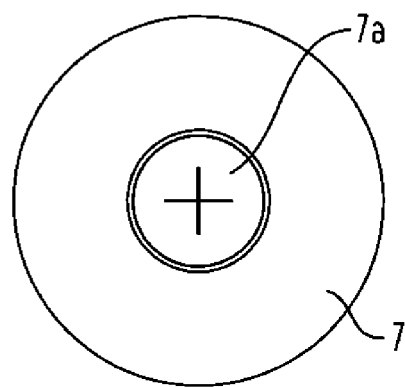
FIG. 3 is an exploded view of the soft cover and its controllable outlet orifice according to an exemplary embodiment of the present invention wherein the controllable outlet orifice is a cross slit.

Referring now to FIG. 3, the controllable outlet orifice 7a is a cross-slit enabling substantially dripless dispensing of the flowable substance. The cross-slit causes the controllable outlet orifice 7a to self close on itself after pressure is released.

The controllable outlet orifice 7a can be formed as desired to provide a spray or a stream of the flowable substance. Alternatively, by selectively dimensioning the controllable outlet orifice 7a, a drop-like amount of the flowable substance can be dispensed, for example if an eye care solution is being dispensed. If a greater amount of the flowable substance is to be dispensed, the controllable outlet orifice 7a can be formed for dispensing a larger quantity of the flowable substance, for example, a eye or nasal solution and/or gel.

Referring now to FIGS. 4A-D, the valve assembly 3 preferably has an inner core 10, an axially extending blind passageway 11, ports 12, a flexible membrane 13, a valve cover 14 with a flange 14a, and a soft cover 7 with a controllable outlet orifice 7a. An over cap 15 is placed over the valve assembly 3 when it is not in use, protecting it from contact with ambient contaminants.

In the valve assembly 3, an axially extending inner core 10 bears against the opening of the reservoir 2 so that flow from the reservoir enters into an axially extending blind passageway 11 in the inner core. The passageway 11 extends for a major portion of the axial length of the inner core. At approximately half the length of the passageway 11, the inner core has a pair of ports 12 extending transversely of the passageway axis from the surface of the passageway to the outer surface of the inner core 10. The inner core 10 is formed of, for example, a rigid plastic material and terminates inwardly of the outlet end of the valve assembly. Furthermore, in exemplary embodiments, upon assembly and filling of the assembly no air is present inside the passageway 11 and the ports 12. It should be noted that additional ports 12 may be located through the inner core 10.

Furthermore, in exemplary embodiments the inner core 10 and the flexible membrane 13 are constructed such that they fit tightly together, for example having very close tolerances which allow for an air-tight seal to be formed between the flexible membrane 13 and the inner core 10. In further exemplary embodiments the molding process for the flexible membrane 13 and the inner core 10, as well as other components described above as sealing against one another is an asymmetric molding process which creates a surface substantially free of defects or seam lines at the areas of contact where sealing occurs. Accordingly, in an exemplary embodiment, very close tolerances between the parts, for example the inner core 10 and flexible membrane 13 and the other parts, are used to provide an optimal seal and operation of the valve assembly.

A flexible membrane 13, such as an elastomeric member, is fitted tightly over the outer surface of the inner core and extends from the opening in the reservoir 2 to the opposite end of the inner core 10. As can be noted in FIGS. 4A-D, the thickness of the membrane is preferably variable along its axial length. In the region of the outlet end of the inner core has, for example, an axially extending continuous uninterrupted end considerably thicker than the remainder of the flexible membrane 13. That is, the band is not separated in the axial direction by axially extending cuts. The thicker end ensures that after the valve has dispensed fluid, as further described below, the valve closes at the end closest to the opening 7a first, therefore preventing any backflow. This is effected by the heavy wall thickness which provides for greater tension. As a result, the flexible membrane 13 exhibits non-uniform tension.

In a further example, in yet other embodiments, the thickness of the membrane may be variable along its axial length and the region surrounding the outlet end of the inner core has, for example, an axially extending continuous uninterrupted annular band considerably thicker than the remainder of the flexible membrane 13. Furthermore, in certain embodiments, the band is not separated in the axial direction by axially extending cuts. Alternatively, the elasticity or durometer of the end of the flexible membrane closest to the valve opening may be varied, for example it may be reduced, such that the end closest to the valve opening seals first when pressure is relieved.

In a further embodiment, flexible membrane 13 and inner core 10 are substantially tapered or substantially conical at the ends closest to the controllable outlet orifice 7a such that the inner core 10 nest into the flexible membrane 13 one another when being assembled by high speed automated production equipment.

At its end adjacent to the opening of the reservoir 2, the flexible membrane 13 has an outwardly extending flange bearing against a flange on the inner core located at the opening from the reservoir.

An axially extending valve cover 14 encircles the flexible membrane 13 and, as shown in the rest position in FIG. 2a, is spaced radially outwardly from the outer surface of the flexible membrane. The end of the valve cover 14 adjacent the reservoir 2 has a radially outwardly extending flange 14a bearing against the flange at the end of the flexible membrane effecting the seal for the valve assembly at the opening from the reservoir 2.

The valve cover 14 is formed, for example, of an inner layer of an elastomeric material extending axially from its flange 14a to and over the outlet end of the valve assembly 3. Elastomeric material forms a soft cover 7 over the outlet end of the valve cover 14 which is particularly advantageous when the valve assembly is used for dispensing an eye care solution. Such a soft cover 7 prevents, for example, any likelihood of harm to the delicate outer surfaces of the eye or surrounding tissue. The soft cover 7 has a controllable outlet orifice 7a for dispensing the flowable substance. The outlet orifice is closed in the rest position of the continuously sealing one way valve assembly and open in the dispensing position.

Referring yet again to FIGS. 4A-D and to FIG. 5, various embodiments of the valve assembly 3 are depicted having variations in the structure of the soft cover 7 as described below.

Figure 4A:
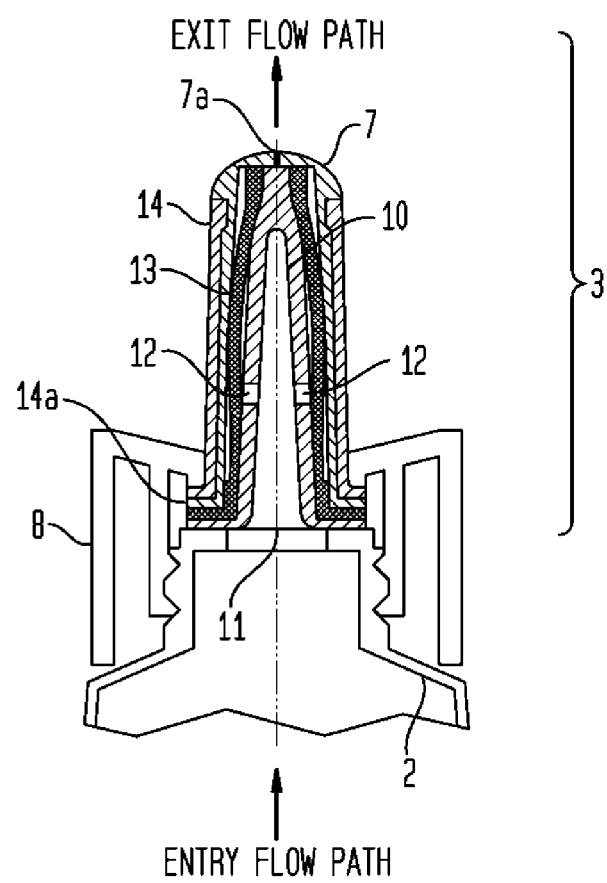
FIG. 4A is an enlarged axially extending partial view of the continuously sealing one way valve assembly with a flat topped soft cover according to an exemplary embodiment of the present invention.

Referring now especially to FIG. 4A, a valve assembly having a flat topped soft cover 7 is provided. The soft cover 7 has a flattened top, which allows for less flowable substance to adhere to the controllable outlet orifice 7a because the flattened top results in a shorter controllable outlet orifice 7a. The soft cover 7 has a controllable outlet orifice 7a which can be formed as desired to provide a spray or a stream of the flowable substance. Furthermore, the controllable outlet orifice 7a can be a cross-slit as shown in FIG. 3. Alternatively, by selectively dimensioning the controllable outlet orifice 7a, a drop-like amount of the flowable substance can be dispensed, for example if an eye care solution or other solution typically delivered in droplet form, is being dispensed. If a greater amount of the flowable substance is to be dispensed, the controllable outlet orifice 7a can be formed for dispensing a larger quantity of the flowable substance, for example by having a larger diameter opening for products such as eye or nasal solutions and/or gels.

Figure 4B:
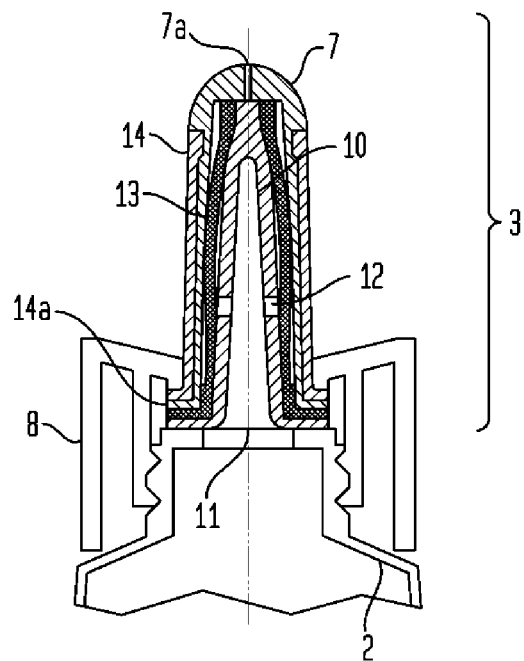
FIG. 4B is an enlarged axially extending partial view of the continuously sealing one way valve assembly with a rounded soft cover according to an exemplary embodiment of the present invention wherein the continuously sealing one way valve assembly is in the rest position.
Figure 4C:
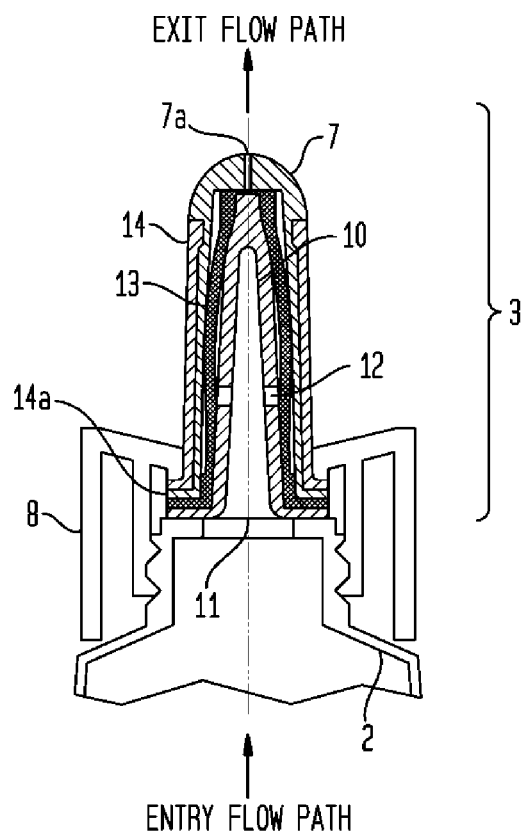
FIG. 4C is an enlarged axially extending partial view of the continuously sealing one way valve assembly with a rounded soft cover according to an exemplary embodiment of the present invention wherein the continuously sealing one way valve assembly is in the dispensing position.

Referring now especially to FIGS. 4B-C, a valve assembly having a rounded soft cover 7 is provided. The soft cover 7 has a rounded top useful for dispensing flowable substance into the outer surfaces of the eye and surrounding tissue or other sensitive body areas. Because the rounded tip lacks sharp edges, damage to the eye or other sensitive tissues is avoided or reduced if incidental contact occurs during administration of the flowable substance. The soft cover 7 has a controllable outlet orifice 7a which can be formed as desired to provide a spray or a stream of the flowable substance. Furthermore, the controllable outlet orifice 7a can be a cross-slit as shown in FIG. 3. Alternatively, by selectively dimensioning the controllable outlet orifice 7a, a drop-like amount of the flowable substance can be dispensed, for example if an eye care solution or other solution typically delivered in droplet form, is being dispensed. If a greater amount of the flowable substance is to be dispensed, the controllable outlet orifice 7a can be formed for dispensing a larger quantity of the flowable substance, for example by having a larger diameter opening for products such as eye or nasal solutions and/or gels.

Figure 4D:
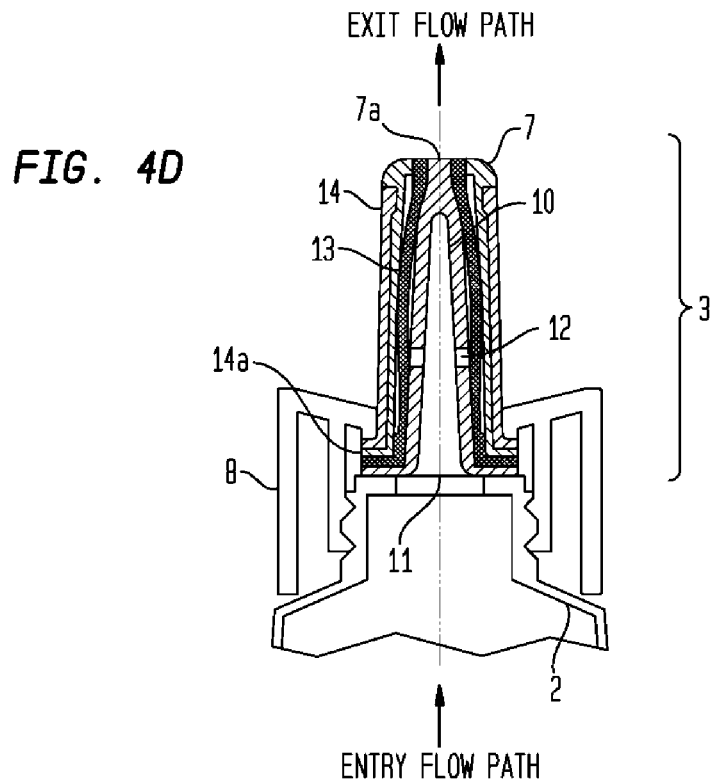
FIG. 4D is an enlarged axially extending partial view of the continuously sealing one way valve assembly where the opening in the soft cover contains a portion of the flexible membrane and inner core of the valve assembly according to an exemplary embodiment of the present invention.

Referring now especially to FIG. 4D, a valve assembly having a flat cover 7 which has an enlarged version of controllable outlet orifice 7a is provided. The enlarged version of controllable outlet orifice 7a is able to accommodate the inner core 10 and flexible membrane 13 and is suitable for dispensing viscous flowable substances such as lotions, creams and emollients, but may also be used for any flowable substance. The enlarged version of controllable outlet orifice 7a allows flowable substance to be dispensed without having to move through two openings—namely the opening at the end of the flexible elastomer 13 and the controllable outlet orifice 7a, since these are now flush.

Figure 5:
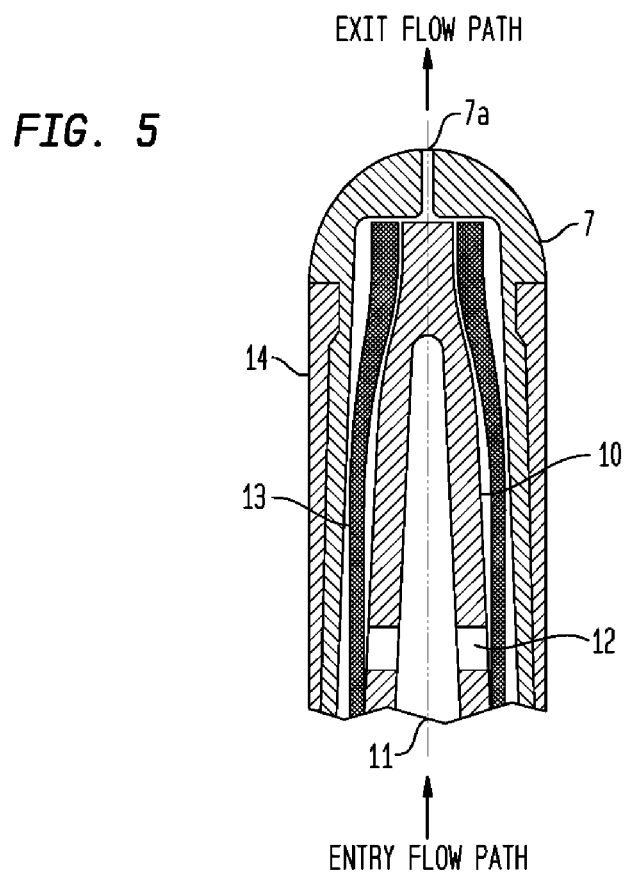
FIG. 5 is an enlarged partial axially extending view of the continuously sealing one way valve assembly shown in FIGS. 4B and 4C according to an exemplary embodiment of the present invention.

Referring now to FIG. 5 the gap formed between inner core 10 and the flexible membrane 13 by the pressurized fluid flowing out of ports 12 can more easily be seen. The controllable outlet orifice 7a in soft cover 7 can also be seen and may for example be a substantially uniform circular bore thought the material of soft cover 7 or may be suitably dimensioned as described in the preceding paragraphs.

Referring now to FIGS. 6A-B, in another embodiment, flowable substance flows through a single port 12 in inner core 10 and expands the flexible membrane 13, swirling around the exterior of inner core 10, and exiting via an outlet port 12a as shown in FIGS. 6A and 6B. This results in the need for less cracking pressure to dispense flowable substance and is particularly advantageous for use with, though not limited to, flowable substances having higher viscosities such as viscoelastic solutions and/or viscoelastic gels. It should be noted that additional ports 12 may be located through the inner core 10.

In exemplary operation, when the flowable substance is to be dispensed, the over cap 15 is removed and pressure is applied to the actuator 2a of the reservoir 2 so that an amount of the flowable substance passes out of the reservoir into the passageway 11 in the inner core 10. The substance flows through the ports 12 and expands the flexible membrane 13 radially outwardly and flows toward the outlet end of the flexible membrane where it exits from the flexible membrane radially inwardly into the controllable outlet orifice 7a in the cover and is dispensed.

When the flowable substance is being dispensed and exits the outlet end of the flexible membrane, it flows radially inward to the controllable outlet orifice 7a which then opens allowing the substance to flow out of the valve assembly. When the flowable substance is dispensed and pressure on the source is withdrawn the controllable outlet orifice 7a closes blocking any backflow into the valve assembly. An over cap 15 is placed over the valve assembly 3 when it is not in use, protecting it from contact with ambient contaminants.

In another embodiment, as depicted in FIGS. 6A and 6B for example, flowable substance flows through a single port 12 in inner core 10 and expands the flexible membrane 13, swirling around the exterior of inner core 10, and exiting via an outlet port 12a as shown in FIGS. 6A and 6B. This results in the need for less cracking pressure to dispense flowable substance and is particularly advantageous for use with, though not limited to, flowable substances having higher viscosities such as viscoelastic solutions and/or viscoelastic gels.

By releasing the pressure on the actuator 2a of the reservoir, the dispensing operation is terminated and the flexible membrane 13 returns inwardly into contact with the outer surface of the inner core 10. The inward movement of the flexible membrane starts at its outlet end because of its increased thickness and affords gradual contact with the outer surface of the inner core, returning any flowable substance through the ports back into the reservoir whereby contaminants cannot enter the reservoir. Dispensing individual portions of the flowable substance can be continued until the reservoir is almost completely emptied. As a result of the structure and operation of the valve assembly, the valve assembly according to an exemplary embodiment of the present invention provides uniform pressure on the valve components via the pressurization of the flowable substance.

In still another exemplary embodiment, for example a spray pump such as that depicted in FIG. 2B, an actuator 17 serves to transfer force to the pump assembly 16 when it is depressed. This in turn compress the reservoir 2, thus providing the force necessary to open the valve assembly and in certain embodiments described above, controllable outlet port 7a, to dispense flowable substance.

Elastomers suitable to form the soft cover 7, the flexible membrane 13 and the valve cover 14 in exemplary embodiments of the present invention include thermoplastic elastomers such as Dynaflex manufactured by GLS Corp., C-Flex manufactured by CPT Inc., or Santoprene manufactured by Advanced Elastomer Systems, Inc. The elastomers, and the materials comprising any of the other components of the device may have integrated, impregnated, otherwise placed within them anti-microbial ingredients such as silver ions contained within a ceramic carrier, such as those supplied by AgION, or sustained-release ionic silver compounds, such as those supplied by Westlake Plastic Technologies which are known to be used in the making of anti-microbial plastics. Furthermore, other anti-microbial suitable for compounding with or coating plastics may be used. Furthermore, the soft cover 7 or the flexible membrane 13 or both could, for example, be positively charged to repel residual flowable substance, coated in for example, Teflon type-plastics, have increased surface tension or be anti-wetting, or any combination of the above so as to repel flowable substance.

In yet other embodiments, including those described above, the durometer of the elastomers can be varied in relation to the viscosity of the flowable substance. For example, assemblies containing substances with comparatively higher viscosities would utilize softer, i.e. lower durometer elastomers, in order to reduce the cracking force needed to dispense flowable substance, whereas lower viscosity flowable substances would utilized harder, i.e. higher durometer elastomers to maintain a strong seal. Likewise, flowable substances containing lubricants would also utilize harder, i.e. higher durometer elastomers to maintain a strong seal.

As described above, the parts of the dispending and delivery device, including the valve assembly may be manufactured to close tolerances such that they form airtight seals and are close fitting ensuring optimal seals and operation of the device.

Opthalmological products or otorhinolarygology products, as described below, may be dispensed where it is important to maintain them free of contaminants from the ambient atmosphere. The flowable characteristics of the material being dispensed determines the type and dimension of the valve assembly.

As mentioned, the flowable substance may be a preservative-free pharmaceutical, such as the opthalmological products or otorhinolarygology products of the examples below, all of which are intended to be maintained free of contaminants from the ambient atmosphere and of preservatives during storage within the reservoir 2. The opthalmological products or otorhinolarygology products of the examples below are amenable to storage and dispensing from reservoirs using the continuously sealing one way valve assembly and delivery system of the present invention.

The following examples provide embodiments describing categories of medical products which are amenable to storage and dispensing from reservoirs using the continuously sealing one way valve assembly and delivery system of the present invention. Preservative-free storage and delivery of these formulations also can be accomplished by providing, for example, multi-dose metered, high barrier and preservative-free systems as described in U.S. Pat. Nos. RE 34,243; 5,092,855; 5,305,783; 5,279,447; 5,305,786; and 5,353,961 all of which are hereby incorporated by reference in their entirety.

EXAMPLES

Example 1

In an exemplary embodiment, preservative free ophthalmic products are amenable to storage and dispensing from reservoirs using the continuously sealing one way valve assembly and delivery system of the present invention. For example eye drops, and preferably those eye drops involved in chronic care, for example, dry eye, glaucoma, allergies and NSAIDs, and also those eye drops intended for acute care, for example during ocular surgery, are amenable to storage and dispensing from reservoirs using the continuously sealing one way valve assembly and delivery system of the present invention. As a further example, those eye drops used to relieve eye fatigue, those eye drops used to relieve dry eye, those eye drops used relieve dry eye due to computer use, television use, or fatigue due to prolonged awake periods are amenable to storage and dispensing from reservoirs using the continuously sealing one way valve assembly and delivery system of the present invention.

Examples of dry eye products can include dry eye products comprised of but not limited to cellulose derivatives, hyaluronan of differing molecular weights including high molecular weight (HMW) alone by itself or in combination with a low molecular weight hyaluronan component (LMW), polyethelene glycol 400 0.4%, propylene glycol 0.3%, glycerin, dextran, polysorbate 80 and mineral oils. Examples of glaucoma products include glaucoma products comprising timolol 0.25%/0.50%, brimonidine tartrate 0.1%, bimatoprost 0.03% and travaprost 0.004%. Examples of allergy products include allergy products comprising olopatadine HCL 0.1% and predisalone acetate 1%. Examples of NSAID products include NSAID products comprising ketorolac 0.5% and diclofenac 0.1%.

Further, in preferred embodiments for use on the eye, a formulation of hyaluronan and demulcents, along with suitable excipients, is stored and dispensed from reservoirs using the continuously sealing one way valve assembly and delivery system of the present invention. Examples and methods of making such formulations are provided below.

Hyaluronan and/or its derivatives, which can be formulated in its sodium, potassium, calcium or other salt forms with concentrations which in certain embodiments may vary from about 0.05 to about 3.0 percent (w/v) and with a molecular weight ranging from about 300,000 daltons to about 7,000,000 daltons in its native form and up to about 25,000,000 daltons in its cross-linked form, are utilized in the present formulations.

Preferably, use of about 10 to about 15 million or about 10 to about 25 million dalton hyaluronan (high molecular weight HA) provides substantial benefits during ocular surgical procedures. Since patients are undergoing surgery, often sedated in some manner, a high molecular weight hyaluronan may be used without the disadvantage of blurring and foreign body sensations or eye irritation from the high molecular weight HA and which provides enhanced benefits. For example, the requirement to repeatedly irrigate the eye during ocular surgery is substantially reduced because the higher molecular weight HA acts as a molecular sponge, storing and releasing more of the demulcents and water. Additionally, the cross-linking present in high molecular weight HA allows a lower concentration of hyaluronan to be used in the formulation. In addition, this type of formulation may be advantageous when used to coat the corneal surface during laser ablation as used in refractive eye surgery. Since blurring and foreign body sensation are not a problem in this type of refractive laser surgery, the use of higher molecular weight HA will prove to be advantageous. Additionally, the cross-linking present in high molecular weight HA allows a lower concentration of hyaluronan to be used in the formulation.

In a preferred embodiment, about 1.4 to about 2.0 or about 1.5 to about 2.0 million dalton hyaluronan provides substantial benefits in formulations for dry eye and other non-surgical uses. For example, side effects such as blurry vision and foreign body sensation as well as irritation are minimized and the effective residence time of each application is increased. This results in less need to reapply product to the eye. Furthermore, using hyaluronan at the aforementioned molecular weights provides improved and prolonged delivery of demulcents and superior hydration of the corneal surface while maintaining the vital elastoviscous properties of the eye drop. Thus the elasticity and viscosity of the formulation is maintained, before, during and after the constant blinking process which aids the coating and recoating of the ocular surfaces of the eye and the inner surface of the eyelid.

In further embodiments, hyaluronan and/or its derivatives in combination with glycerin and/or any other demulcent components acts as an enhanced mucoadhesive, providing increased residence time and enhanced coating.

In still further embodiments, viscoadaptive formulations may be used to deliver drugs in combination with a preservative-free delivery pump or device to the ocular tissues for the purpose of enhanced bioavailability and increased residence time. For example, the residence time of antibiotics on the ocular tissues can be increased from minutes to hours. Examples of drugs deliverable in this manner include anti-glaucoma, anti-allergy, steroids, antibiotics, NSAIDs, inflammatory, anti-inflammatory, antifungal and other drugs which are delivered topically to ocular tissue.

Such a viscoadaptive formulation may be used for the treatment of dry eye conditions due to noxious environmental conditions, surgery, computer fatigue, air travel, heating, iatrogenic dry eye, dry eye syndromes, trauma, medications and disease.

Embodiments of the present invention provide several surprising benefits, including for example, superior coating, enhanced mucoadhesive surface tension to ocular surfaces, longer residence time, superior patient comfort, superior moisturizing, clear visibility of the surgical field for surgeons, superior and more symmetric coating of the corneal surface during laser refractive surgery to allow selective ablation of corneal irregularities and preservative-free multi-dose, multi-use dispensing of the product.

For example, embodiments of the invention provide superior coating of the corneal surface of the eye and the conjunctiva with a longer in vivo residence time due at least in part to the novel combination of hyaluronan having a particular size range and/or its derivatives with other demulcent component(s), including but not limited to glycerin.

Furthermore, superior patient comfort is provided due to the elastoviscosity of the hyaluronan and/or its derivative components which is achieved by the novel sizes and concentrations of the hyaluronan used in the embodiments.

Additionally, superior moisturizing due to the hyaluronan and or its derivative components because the novel sizes and concentrations of the hyaluronan used in the embodiments allow the hyaluronan to act as a molecular sponge, soaking up and releasing demulcents and water as the patient blinks. Furthermore, the embodiments allow for greater clarity of patient vision because lower concentrations of the hyaluronan component are used. An additional surprising benefit is the promotion of a clear field of view for surgeons when the compositions are used during surgery as a viscoadaptive fluid corneal shield (eye drop) on the surface of the eye and smoother coverage of the corneal surface during laser refractive surgery.

Still further, a preservative-free delivery system which is capable of containing and delivering multiple doses of the eye drops, while keeping the formulation free from contamination and/or spoilage has been developed, eliminating the costly need for and waste associated with single-use unit dosing.

Such viscoadaptive eye drops are thus particularly well adapted for the treatment of dry eye conditions due to, for example, noxious environmental conditions, surgery, computer fatigue, air travel, heating, iatrogenic dry eye, dry eye syndromes, trauma, disease, intra and post-surgical use.

In certain embodiments a visco adaptive eye drop according to the present invention may include combinations of cellulose derivatives, dextrans, gelatin, polyols, polyvinyl alcohols and povidone.

Cellulose derivatives include, but are not limited to, for example, carboxymethylcellulose sodium, hydroxyethylcellulose, hydroxypropylmethylcellulose, and methylcellulose. Cellulose derivatives may comprise from about 0.05 to about 2.5 percent, by weight of the final formulation.

Dextran or dextran derivatives may also be included. For example, Dextran 70 may be used in formulations according to the present invention. Typically concentrations of about 0.1 percent dextran may be used when another polymeric demulcent agent and delivery system of the present invention is used.

Gelatin also may be included. When included, gelatin may comprise about 0.01 percent, by weight.

Polyols may include glycerin, Polyethylene Glycol 300, Polyethylene Glycol 400 Polysorbate 80, and propylene glycol. Typically, concentrations of polyols comprise from about 0.05 to about 1 percent by weight of the composition. Further, glycerin may also be provided from about 0.05% to about 0.5%

Polyvinyl alcohol (PVA), typically in concentrations ranging from about 0.1 to about 4 percent and povidone (PVP) in typically in concentrations ranging from 0.1 to 2 percent, also may be included.

Weight percentages referred to above may vary under certain conditions as will be appreciated by a person skilled in the art provided with the present disclosure.

In certain embodiments phosphate or other buffering agents may be incorporated in the formulation to maintain a pH varying from about 6.0 to about 8.0. Sodium chloride or other salts may be incorporated in certain compositions to maintain osmolality ranging from about 130 to about 380 mOsmol/Kg. Water may be used to provide an aqueous medium.

In certain embodiments compositions may be formulated with or without preservatives depending on the packaging of the final product in order to maintain sterility. Some packaging options include, for example: single unit-dose reservoirs without preservatives, multi-dose reservoirs with preservatives and multidose reservoirs (which do not allow air intake) without preservatives and syringes or ampoules.

In certain embodiments, the hyaluronan used has a molecular weight ranging from about 1.4 million to about 2.0 million daltons.

In certain embodiments, useful in ocular surgery, as described above, hyaluronan is provided with a molecular weight ranging from about 2 to about 15 million daltons, or preferably from about 10 to about 25 million daltons or more preferably from about 10 to about 15 million daltons.

In certain embodiments hyaluronan is present in a concentration of about 0.05 to about 0.5%.

In certain embodiments biofermented hyaluronan is provided, eliminating the need to use an animal source for the molecule. This reduces the risk of viral or other biological contamination of the hyaluronan.

In certain embodiments demulcents, also known as dopants, are provided in conjunction with hyaluronan. For example, polyols, PVA and PVP may be used as dopants because they are less viscous and therefore less likely to cause discomfort or blurred vision and in addition provide longer residence time on the cornea. Therefore, in certain embodiments polyols, would be used for contact lens comfort drops, day time and night time drops, or for mild or moderate KCS or dry eye, as well as in veterinary applications for animals which depend on their visual acuity during their active periods and for night time relief from the symptoms of dry eye as well as for use during laser refractive surgery.

In certain embodiments, cellulose derivatives would be used as dopants in conjunction with hyaluronan. For example, cellulose derivatives, which are more viscous, would be used in bed time, intra-operative, post surgical and moderate to severe KCS as well as in veterinary applications where the animal does not primarily rely on its visual acuity.

In certain embodiments compositions may be formulated in an aqueous mixture and/or solution as described in the following table:

TABLE 1

| Ingredient | Quantity |
|---|---|
| Hyaluronan | 1.5 mg/mL |
| Glycerin | 2.0 mg/mL |
| NaCl | 8.5 mg/mL |
| Dibasic Phosphate | 0.27 mg/mL |
| Monobasic Phosphate | 0.04 mg/mL |

Example 1.1

In one example, the composition of Table 1 is used to lubricate the eye of a patient undergoing ocular laser refractive surgery and other ocular surgeries. Examples of ocular surgery include corneal transplantation, cataract, intraocular lens implantation, glaucoma and retinal surgery. During the surgery the surgical staff do not have to irrigate and re-irrigate the eye as often as they would have had they used any available substitute composition.

Example 1.2

In another example, the composition of Table 1 is applied to the eye of a patient who presents with dry eye syndrome or other conditions of eye dryness or mild, moderate or severe irritation due to disease, noxious environmental conditions, insufficiency of natural tears or work-related conditions such as prolonged use with computers which retards or diminishes the natural blinking process leading to poor lubrication, dryness and irritation. The patient's dry eye symptoms are relieved and the patient need not reapply the eye drop as often as they would have had they used any available substitute composition.

Example 1.3

In yet another example, the composition of Table 1 is applied to the eye of a patient suffering from dry eye due to airborne, environmental, contact lens wear or allergy related reasons. The patient's dry eye symptoms are relieved and the patient need not reapply the eye drop as often as they would have had they used any available substitute composition.

Thus formulations combining hyaluronan and demulcents and/or preservative-free storage and delivery of the these formulations are provided for patients undergoing ocular surgery or suffering from dry eye irritation and related dryness conditions are provided with a preservative-free viscoadaptive eye drop having improved viscosity and delivery of lubricating demulcents to the eye. Furthermore, these embodiments are also generally useful for ear, nose and throat applications.

Example 2

In an exemplary embodiment, preservative-free otorhinolaryngological products are amenable to storage and dispensing from reservoirs using the continuously sealing one way valve assembly and delivery system of the present invention. For example, nasal medicines, and preferably nasal sprays, external ear creams, ear drops, steroid ear drops, antibiotic ear drops, nose drops, and nose drops comprising phenylephrine 0.25% and pseudoephedrine 30 mg, are amenable to storage and dispensing from reservoirs using the continuously sealing one way valve assembly and delivery system of the present invention.

Further, in preferred embodiments for use in the nasal and sinus cavities, a formulation of hyaluronan and demulcents, along with suitable excipients, is stored and dispensed from reservoirs using the continuously sealing one way valve assembly and delivery system of the present invention. Examples, and methods of making such formulations are provided below:

Hyaluronan and/or its derivatives which can be formulated in its sodium, potassium, calcium, zinc or other salt forms with concentrations which in certain embodiments may vary from about 0.05 to about 3.0 percent and with a molecular weight ranging from about 300,000 daltons to about 7,000,000 daltons in its native form and up to about 25,000,000 daltons in its cross-linked form are utilized in the present formulations.

Preferably, a viscoadaptive formulation including 10 to 15 million or 10 to 25 million dalton hyaluronan (high molecular weight HA) in combination with a low molecular weight demulcent, described below, provides substantial benefits during or after nasal or trans-nasal sinus surgical procedures. For example, a visco adaptive high molecular weight HA formulation may be physically pumped into the nasal or sinus cavity(ies) of the patient, eliminating the difficulty associated with administering nasal moisturizing and/or anti-adhesion fluids to the patient via traditional methods. Additionally, the cross-linking present in high molecular weight HA allows a lower concentration of hyaluronan to be used in the formulation.

In a preferred embodiment, 1.0 to 2.0 or 1.5 to 2.0 million dalton hyaluronan provides substantial benefits in formulations for dry nose and other non-surgical and post-surgical uses. For example, the negative effect of repeated applications of saline solutions to maintain a minimal level of comfort and moisture are minimized because the effective residence time is increased. Less applications needed to maintain comfort, moisture, hydration and protection is a significant physical and clinical benefit of the invention.

Such viscoadaptive formulations may be used for the treatment of dry nose, sneezing and/or irritation caused by, for example, colds, influenza, allergies, dust, smoke, air pollution, air conditioning, winter heating, high altitudes, travel, oxygen therapy, dryness caused by certain medications, iatrogenically induced dry nose and dry nose caused by surgery and anaesthesia.

In further embodiments, hyaluronan and/or its derivatives in combination with glycerin and/or any other demulcent components acts as an enhanced mucoadhesive, providing increased residence time and enhanced coating.

In still further embodiments, viscoadaptive formulations may be used to deliver drugs, via a preservative-free delivery pump or device, to the nasal tissues by providing enhanced bioavailability and increased residence time, in a magnitude of up to 10 times or more. For example, the residence time of antibiotics on the nasal tissue would be increased from minutes to hours. Examples of drugs deliverable in this manner include anti-allergy, steroids, antibiotics, NSAIDs, inflammatory drugs, anti-inflammatory drugs, antifungal drugs and other drugs which are delivered directly to nasal or sinus tissue.

In certain embodiments a viscoadaptive nasal fluid according to the present invention may include combinations of cellulose derivatives, dextrans, gelatin, polyols, polyvinyl alcohol and povidone.

Embodiments of the present invention provide several surprising benefits, including for example, superior coating, enhanced mucoadhesive tension to nasal and sinus surfaces, longer residence time, superior moisturizing, easier application, more even coating of the nasal and sinus surfaces during and after surgery and preservative-free multi-dose, multi-use dispensing of the product.

Additionally, a viscoadaptive high molecular weight HA formulation may be physically pumped into the patient, eliminating the difficulty associated with administering nasal moisturizing fluids to the patient via traditional methods and providing more even coating of the nasal and sinus surfaces, including inaccessible cavities and tissue surfaces during surgery.

Further, a preservative-free delivery system which is capable of containing and delivering multiple doses of the nasal moisturizing fluid, while keeping the formulation free from contamination and/or spoilage has been developed, eliminating the costly need for and waste associated with single use unit dosing.

In certain embodiments a viscoadaptive nasal fluid according to the present invention may include combinations of cellulose derivatives, dextrans, gelatin, polyols, polyvinyl alcohols and povidone.

Cellulose derivatives include, but are not limited to, for example, carboxymethylcellulose sodium, hydroxyethylcellulose, hydroxypropylmethylcellulose, and methylcellulose. Cellulose derivatives may comprise from about 0.0.5 to about 2.5 percent, by weight of the final formulation.

Dextran or dextran derivatives may also be included. For example, Dextran 70 may be used in formulations according to the present invention. Typically concentrations of about 0.1 percent dextran may be used when another polymeric demulcent agent and delivery system of the present invention is used.

Gelatin also may be included. When included, gelatin may comprise about 0.01 percent, by weight.

Polyols may include glycerin, Polyethylene Glycol 300, Polyethylene Glycol 400 Polysorbate 80, and propylene glycol. Typically, concentrations of polyols comprise from about 0.05 to about 1 percent by weight of the composition. Further, glycerin may be provided from about 0.05% to about 0.5% by weight.

Polyvinyl alcohol (PVA), typically in concentrations ranging from about 0.1 to about 4 percent and povidone (PVP), typically in concentrations ranging from about 0.1 to about 2 percent, also may be included.

Weight percentages referred to above may vary under certain conditions as will be appreciated by a person skilled in the art provided with the present disclosure.

In certain embodiments phosphate or other buffering agents may be incorporated in the formulation to maintain a pH varying from about 5.0 to about 8.0, more preferably about 6.0 to about 8.0. Sodium chloride or other salts may be incorporated in certain compositions to maintain osmolality ranging from about 270 to about 350 mOsmol/kg. Water may be used to provide an aqueous medium.

In certain embodiments compositions may be formulated with or without preservatives depending on the packaging of the final product in order to maintain sterility. Some packaging options include, for example: single unit-dose reservoirs without preservatives, multi-dose reservoirs with preservatives and multidose reservoirs (which do not allow air intake) without preservatives and syringes or ampoules.

In certain embodiments, the hyaluronan used has a molecular weight ranging from about 1.0 million to about 2.0 million daltons, or about 1.4 million to about 2.0 million daltons.

In certain embodiments, useful in nasal or sinus surgery, as described above, hyaluronan is provided with a molecular weight ranging from about 10 to about 25 million daltons, more preferably from about 10 to about 15 million daltons.

In certain embodiments hyaluronan is present in a concentration of about 0.05 to about 0.5%. In still other embodiments, useful for surgical or post surgical applications, hyaluronan is present in a concentration of about 0.15% to about 0.5%. In yet another embodiment, useful for daily use for treatment of dry nose, hyaluronan is present in a concentration of about 0.15 to about 0.3% or of about 0.05 to about 0.5%.

Weight percentages referred to above may vary under certain conditions as will be appreciated by a person skilled in the art provided with the present disclosure.

In certain embodiments compositions may be formulated with or without preservatives depending on the packaging of the final product in order to maintain sterility. Some storage and/or delivery options include, for example: single unit-dose reservoirs without preservatives, multi-dose reservoirs with preservatives and multidose reservoirs (which do not allow air intake) without preservatives and syringes or ampoules.

In certain embodiments biofermented hyaluronan is provided, eliminating the need to use an animal source for the molecule. This reduces the risk of viral or other biological contamination of the hyaluronan.

In certain embodiments demulcents, also known as dopants, are provided in conjunction with hyaluronan. For example, polyols, PVA and PVP may be used as dopants because they are less viscous and therefore less likely to cause discomfort and in addition provide longer residence time on the nasal tissue.

In certain embodiments, cellulose derivatives would be used as dopants in conjunction with hyaluronan. For example, cellulose derivatives, which are more viscous, would be used in bed time, intra-operative, post-surgical and moderate to severe dry nose conditions.

In certain embodiments compositions may be formulated in an aqueous mixture and/or solution as described in the following table:

TABLE 1

| Ingredient | Quantity |
| --- | --- |
| Hyaluronan | 1.5 mg/mL |
| Glycerin | 2.0 mg/mL |
| NaCl | 8.5 mg/mL |
| Dibasic Phosphate | 0.27 mg/mL |
| Monobasic Phosphate | 0.04 mg/mL |

In certain embodiments hyaluronan and/or its derivatives may be delivered separately or in combination with other demulcents as a viscoadaptive fluid in a pumping device, utilizing the one-way valve and delivery system of the present invention, for direct application to the nostril(s) to optimize ease of use and hygienic application without direct contact with the affected area. Further, this product also can be delivered in a tube-type configuration or a reservoir utilizing the one-way valve and delivery system of the present invention. Still further, the use of a pumping device offers superior hygienic covering of the affected area and ease of use without the need to directly contact the affected area. Therefore, embodiments of the invention also relate to the use of hyaluronan and/or its derivatives either separately or in combination with other demulcents in a pumping device specifically for intra-nasal and trans-nasal indications.

Embodiments of the present invention provide several surprising benefits, including, for example superior coating, superior patient comfort, superior moisturizing, superior hydration and preservative-free multi-dose, multi-use dispensing of the product.

For example, embodiments of the invention provide superior coating of the nasal and sinus tissue surfaces with a longer in vivo residence time due at least in part to the novel combination of hyaluronan and/or its derivatives having the particular size ranges, described above with other demulcent component(s), including but not limited to glycerin.

Furthermore, superior patient comfort is provided due to the elastoviscosity of the hyaluronan and/or its derivative components which is achieved by the novel sizes and concentrations of the hyaluronan used in the embodiments.

Additionally, superior moisturizing due to the hyaluronan and or its derivative components is provided because the novel sizes and concentrations of the hyaluronan used in the embodiments allow the hyaluronan to act as a molecular sponge, soaking up and releasing demulcents and water as needed by the tissue.

Still further, a preservative-free delivery system which is capable of containing and delivering multiple doses of the nasal fluids, while keeping the formulation free from contamination and/or spoilage has been developed, eliminating the costly need for and waste associated with single use unit dosing.

Such viscoadaptive nasal fluids are thus particularly well adapted for the treatment of dry nose conditions due to, for example, colds, influenza, allergies, dust, smoke, air pollution, air conditioning, winter heating, high altitudes, travel, oxygen therapy, dryness caused by certain medications and iatrogenically induced dry nose and dry nose caused by surgery and anesthesia.

Example 2.1

The composition of Table 1 is applied to the nasal or sinus passages of a patient undergoing nasal or sinus surgery. During the surgery the surgeon may have considerably less difficulty in applying the moisturizing fluid to nasal and sinus cavities. Additionally, the viscoadaptive solution has a superior residence time on nasal tissue, which will allow for longer coating, moisturizing, lubricating and protection of delicate nasal tissue and to surgically altered or cut nasal tissue to prevent unwanted postoperative adhesions of tissue surfaces especially in the presence of residual blood following surgery.

Example 2.2

The composition of Table 1 is applied to the ear passages of a patient undergoing middle or inner surgery of the ear. During the surgery, the surgeon may have considerably less difficulty in applying the moisturizing fluid to the cavities and surfaces of the ear. Also, the viscoadaptive solution has a superior residence time on tissue to allow for greater moisturizing, protection, lubrication and to prevent unwanted adhesions of tissue during the postoperative period. In this manner the viscoadaptive solution can facilitate the healing process by avoiding unwanted post-operative surgical adhesion of tissues, for example in the presence of residual blood remaining post-surgery.

Example 2.3

The composition of Table 1 is applied to the nasal or sinus passages of a patient following nasal or sinus surgery. The patient's dry nose symptoms are relieved and the patient need not reapply the nasal fluid as often compared to saline or other nasal solutions that exhibit different physical properties with less residence time.

Example 2.4

The composition of Table 1 is applied to the nasal or sinus passages of a patient suffering from dry nose due to airborne, environmental, certain medications or allergy related reasons. The patient's dry nose symptoms are relieved and the patient need not reapply the nasal fluid as often as they would have had they used any available substitute composition.

Thus formulations combining hyaluronan and demulcents and/or preservative-free storage and delivery of the these formulations are provided such that patients suffering from dry nasal conditions are provided with a preservative-free viscoadaptive nasal fluid, and device for administering the same, having improved, longer lasting moisturizing, protecting and lubricating properties. Furthermore, these embodiments are also generally useful for ear, nose, mouth and throat as well as vaginal applications where a moisturizing fluid is needed.

Although the system is designed for use with various preservative free formulations it may also be used with formulations which are not preservative free.

The invention claimed is:

1. A continuously sealing one way valve assembly and delivery system for dispensing a flowable substance, comprising: a source for storage of the flowable substance, the source having an opening;
a valve assembly coupled to the opening of the source, said valve assembly including
(i) an inner core having an inlet opening for receiving the flowable substance into a passageway and at least one port opening from the passageway,
(ii) a hollow flexible membrane having a first end and a second end, the first end being thicker than the second end,
wherein the hollow flexible membrane is fitted over an outer surface of the inner core and when the flowable substance is placed under pressure the flowable substance exits through the at least one port opening and expands said membrane outwardly from said outer surface of said inner core;
a cover enclosing the flexible membrane and having an outlet orifice for dispensing the flowable substance from the valve assembly when pressure is applied to the flowable substance,
wherein when the pressure on the flowable substance is released, the first end of the hollow flexible membrane moves back into tightly fitting contact with the outer surface of the inner core before the remainder of the hollow flexible membrane moves back into tightly fitting contact with the outer surface of said inner core, and
wherein the source is filled with a preservative free eye care or nasal care product comprising: hyaluronan or derivatives of hyaluronan.

2. A continuously sealing one way valve assembly and delivery system as set forth in claim 1, wherein the hollow flexible membrane has an axially extending uninterrupted continuous band at the first end of the hollow flexible membrane and encircling the core.

3. A continuously sealing one way valve assembly and delivery system as set forth in claim 1, wherein said membrane has a radially outwardly extending flange at the second end thereof adjacent to the passageway of the inner core, and the cover also has a radially outwardly extending flange pressing the flange on the membrane into fluid tight contact with a radially outwardly extending flange at the passageway opening into the inner core.

4. A continuously sealing one way valve assembly and delivery system as set forth in claim 3, wherein a collar and connector member on the source secure the valve assembly to the source.

5. A continuously sealing one way valve assembly and delivery system as set forth in claim 4, wherein the connector member is a threaded screw which mates to the collar.

6. A continuously sealing one way valve assembly and delivery system as set forth in claim 4, wherein a collar and connector member on the source secure the valve assembly to the source and effect a positive lock preventing opening of the source.

7. A continuously sealing one way valve assembly and delivery system as set forth in claim 1, wherein the outlet orifice in the cover is arranged so that it can dispense a selected quantity of the flowable substance.

8. A continuously sealing one way valve assembly and delivery system as set forth in claim 1, wherein the outlet orifice in the cover is formed of a soft material.

9. A continuously sealing one way valve assembly and delivery system as set forth in claim 1, wherein the outlet orifice in the cover is formed of a flexible material.

10. A continuously sealing one way valve assembly and delivery system as set forth in claim 1, wherein the cover is formed of an inner axially extending flexible member laterally enclosed by an axially extending rigid plastic shell.

11. A continuously sealing one way valve assembly and delivery system as set forth in claim 1, wherein an overcap is arranged to fit over and form a seal with said valve assembly sufficient to prevent external contamination from entering the valve assembly during storage.

12. A continuously sealing one way valve assembly and delivery system as set forth in claim 1, wherein at least two ports extend from the passageway through the inner core and to the inner surface of the flexible membrane.

13. A continuously sealing one way valve assembly and delivery system as set forth in claim 1, wherein the source comprises a collapsible reservoir reducible in volume in proportion as the flowable substance is dispensed from the collapsible reservoir.

14. A continuously sealing one way valve assembly and delivery system as set forth in claim 13, wherein said collapsible reservoir is one of a bellows, a tube and an internal bag.

15. A continuously sealing one way valve assembly and delivery system as set forth in claim 1, wherein an axially extending housing laterally encloses the source.

16. A continuously sealing one way valve assembly and delivery system as set forth in claim 15, wherein the housing has a slot extending in the axial direction for applying dispensing pressure to an actuator of the collapsible reservoir.

17. A continuously sealing one way valve assembly and delivery system as set forth in claim 1, wherein the cover has a closed outlet orifice which opens for dispensing the flowable substance from the cover when dispensing pressure is applied to the source.

18. A continuously sealing one way valve assembly and delivery system, as set forth in claim 17, wherein the outlet orifice in the cover is impervious to the flowable substance and does not retain the flowable substance inwardly of the outlet orifice.

19. A continuously sealing one way valve assembly and delivery system as set forth in claim 1 wherein the inner core is connected to a pump assembly and to an actuator such that flowable substance is dispensed from the outlet orifice when the actuator is depressed.

20. A one-way valve assembly and delivery system of claim 1, wherein the source is filled with a preservative free eye care product comprising: hyaluronan or derivatives of hyaluronan and one or more demulcents.

21. A one-way valve assembly and delivery system of claim 20, wherein the hyaluronan or derivatives of hyaluronan range in size from about 300,000 daltons to about 7,000,000 daltons.

22. A one-way valve assembly and delivery system of claim 20, wherein the hyaluronan or derivatives of hyaluronan range in size from about 1.4 million daltons to about 2.0 million daltons.

23. A one-way valve assembly and delivery system of claim 20, wherein the hyaluronan or derivatives of hyaluronan range in size from about 2 million daltons to about 15 million daltons.

24. A one-way valve assembly and delivery system of claim 20, wherein the hyaluronan or derivatives of hyaluronan range in size from about 10 million daltons to about 15 million daltons.

25. A one-way valve assembly and delivery system of claim 20, wherein the hyaluronan or derivatives of hyaluronan range in size from about 10 million daltons to about 25 million daltons.

26. A one-way valve assembly and delivery system of claim 20, wherein the hyaluronan or derivatives of hyaluronan are present at about 0.05-0.5%.

27. A one-way valve assembly and delivery system of claim 20, wherein the hyaluronan or derivatives of hyaluronan are present at about 0.05-3%.

28. A one-way valve assembly and delivery system of claim 20, wherein the hyaluronan or derivatives of hyaluronan are obtained from biofermentation.

29. A one-way valve assembly and delivery system of claim 20, wherein the source is filled with a preservative free eye care product comprising: hyaluronan or derivatives of hyaluronan, one or more demulcents and a product selected from one or more of the following: timolol 0.25%/0.50%, brimonidine tartrate 0.1%, bimatoprost 0.03% and travaprost 0.004%.

30. A one-way valve assembly and delivery system of claim 20, wherein the source is filled with a preservative free eye care product comprising: hyaluronan or derivatives of hyaluronan, one or more demulcents and a product selected from one or more of the following: olopatadine HCL 0.1% and prednisolone acetate 1%.

31. A one-way valve assembly and delivery system of claim 20, wherein the source is filled with a preservative free eye care product comprising: hyaluronan or derivatives of hyaluronan, one or more demulcents and a product selected from one or more of the following: ketorolac 0.5% and diclofenac 0.1%.

32. A one-way valve assembly and delivery system of claim 20, wherein the demulcent is selected from one or more of the following: cellulose derivatives, dextrans, gelatin, polyols, polyvinyl alcohols and providone.

33. A one-way valve assembly and delivery system of claim 1, wherein the source is filled with a preservative free nasal care product comprising: hyaluronan or derivatives of hyaluronan and one of more demulcents.

34. A one-way valve assembly and delivery system of claim 33, wherein the hyaluronan or derivatives of hyaluronan range in size from about 1.4 million daltons to about 2.0 million daltons.

35. A one-way valve assembly and delivery system of claim 33, wherein the hyaluronan or derivatives of hyaluronan range in size from about 1 million daltons to about 2 million daltons.

36. A one-way valve assembly and delivery system of claim 33, wherein the hyaluronan or derivatives of hyaluronan range in size from about 10 million daltons to about 15 million daltons.

37. A one-way valve assembly and delivery system of claim 33, wherein the hyaluronan or derivatives of hyaluronan range in size from about 10 million daltons to about 25 million daltons.

38. A one-way valve assembly and delivery system of claim 33, wherein the hyaluronan or derivatives of hyaluronan are present at about 0.05-0.5%.

39. A one-way valve assembly and delivery system of claim 33, wherein the hyaluronan or derivatives of hyaluronan are present at about 0.15-3%.

40. A one-way valve assembly and delivery system of claim 33, wherein the hyaluronan or derivatives of hyaluronan are present at about 0.15-0.5%.

41. A one-way valve assembly and delivery system of claim 33, wherein the hyaluronan or derivatives of hyaluronan are obtained from biofermentation.

42. A one-way valve assembly and delivery system of claim 33, wherein the source is filled with a preservative free eye care product comprising: hyaluronan or derivatives of hyaluronan, one or more demulcents and a product selected from one or more of the following: timolol 0.25%/0.50%, brimonidine tartrate 0.1%, bimatoprost 0.03% and travaprost 0.004%.

43. A one-way valve assembly and delivery system of claim 33, wherein the source is filled with a preservative free eye care product comprising: hyaluronan or derivatives of hyaluronan, one or more demulcents and a product selected from one or more of the following: olopatadine HCL 0.1% and prednisolone acetate 1%.

44. A one-way valve assembly and delivery system of claim 33, wherein the source is filled with a preservative free eye care product comprising: hyaluronan or derivatives of hyaluronan, one or more demulcents and a product selected from one or more of the following: ketorolac 0.5% and diclofenac 0.1%.

45. A one-way valve assembly and delivery system of claim 33, wherein the demulcent is selected from one or more of the following: cellulose derivatives, dextrans, gelatin, polyols, polyvinyl alcohols, polysorbate 80 and providone.

46. A continuously sealing one way valve assembly and delivery system as set forth in claim 1, wherein the continuously sealing one way valve assembly and delivery system can dispense multiple doses of preservative-free product.

47. A continuously one way valve assembly and delivery system for dispensing a flowable substance, comprising:
a source for storage of the flowable substance, the source having an opening; a valve assembly coupled to the opening of the source, said valve assembly including
(i) an inner core having an inlet opening for receiving the flowable substance into a passageway and at least one port opening from the passageway,
(ii) a hollow flexible membrane having a first end and a second end, the first end being thicker than the second end,
wherein the hollow flexible membrane is fitted over an outer surface of the inner core and when the flowable substance is placed under pressure the flowable substance exits through the at least one port opening and expands said membrane outwardly from said outer surface of said inner core;
a cover enclosing the flexible membrane and having an outlet orifice for dispensing the flowable substance from the valve assembly when pressure is applied to the flowable substance,
wherein when the pressure on the flowable substance is released, the first end of the hollow flexible membrane moves back into tightly fitting contact with the outer surface of the inner core before the remainder of the hollow flexible membrane moves back into tightly fitting contact with the outer surface of said inner core, and
wherein the source is filled with a preservative free eye care or nasal care product comprising: hyaluronan or derivatives of hyaluronan and one or more demulcents.

48. A continuously sealing one way valve assembly and delivery system for dispensing a flowable substance, comprising: a source for storage of the flowable substance, the source having an opening;
a valve assembly coupled to the opening of the source, valve assembly including
(i) an inner core having an inlet opening for receiving the flowable substance into a passageway and at least one port opening from the passageway,
(ii) a hollow flexible membrane having a first end and a second end, the first end being thicker than the second end,
wherein the hollow flexible membrane is fitted over an outer surface of the inner core and when the flowable substance is placed under pressure the flowable substance exits through the at least one port opening and expands said membrane outwardly from said outer surface of said inner core;
a cover enclosing the flexible membrane and having an outlet orifice for dispensing the flowable substance from the valve assembly when pressure is applied to the flowable substance,
wherein when the pressure on the flowable substance is released, the first end of the hollow flexible membrane moves back into tightly fitting contact with the outer surface of the inner core before the remainder of the hollow flexible membrane moves back into tightly fitting contact with the outer surface of said inner core, and
wherein the source is filled with a preservative free eye care or nasal care product comprising: hyaluronan or derivatives of hyaluronan and one or more demulcents.

49. A delivery system comprising:
a source for storage of the flowable substance, the source having an opening;
a valve assembly coupled to the opening of the source, said valve assembly including
(i) an inner core having an inlet opening for receiving the flowable substance into a passageway and at least one port opening from the passageway,
(ii) a hollow flexible membrane having a first end and a second end, the first end being thicker than the second end, wherein the hollow flexible membrane is fitted over an outer surface of the inner core and when the flowable substance is placed under pressure the flowable substance exits through the at least one port opening and expands said membrane outwardly from said outer surface of said inner core;

a cover enclosing the flexible membrane and having an outlet orifice for dispensing the flowable substance from the valve assembly when pressure is applied to the flowable substance, wherein when the pressure on the flowable substrate is released, the first end of the hollow flexible membrane moves back into tightly fitting contact with the outer surface of the inner core before the remainder of the hollow flexible membrane moves back into tightly fitting contact with the outer surface of said inner core, and wherein the source is filled with a preservative free eye care or nasal care product comprising: hyaluronan or derivatives of hyaluronan.

* * * * *